United States Patent [19]

Caruso et al.

[11] 4,312,866

[45] Jan. 26, 1982

[54] USE OF RIFAMYCIN SV AND ITS RELATED SALTS IN THE TREATMENT OF RHEUMATOID ARTHRITIS, AND RELATED FORMULATIONS SUITED FOR THE PURPOSE

[75] Inventors: Innocenzo Caruso; Franco Montrone, both of Milan; Luigi Molteni, Malnate, all of Italy

[73] Assignee: Dr. L. Zambeletti S.p.A., Milan, Italy

[21] Appl. No.: 166,587

[22] Filed: Jul. 7, 1980

[30] Foreign Application Priority Data

Jul. 10, 1979 [IT] Italy ............................. 24227 A/79
Jun. 13, 1980 [IT] Italy ............................. 22778 A/80

[51] Int. Cl.³ .................. A61K 31/395; C07D 498/08
[52] U.S. Cl. .............................. 424/244; 260/239.3 P
[58] Field of Search ................. 260/239.3 P; 424/244

[56] References Cited

FOREIGN PATENT DOCUMENTS 924472  4/1963  United Kingdom ............. 260/239.3

OTHER PUBLICATIONS

Vogel "Practical Organic Chemistry", Third Edition, 1956, (Wiley) pp. 122–145.
Chemical Abstracts, vol. 55, Col. 19135, (1961), abstracting Sensi et al., "Farmaco(Pavia), Ed. sci.", vol. 16 (1961) pp. 165–180.

*Primary Examiner*—Robert T. Bond
*Attorney, Agent, or Firm*—Bucknam and Archer

[57] ABSTRACT

The invention concerns new salts of rifamycin SV and a new use of rifamycin SV in the treatment of rheumatoid arthritis and analogous affections, by intra-articular injection of the sodium salt of rifamycin SV or, better, of salts of said anti-biotic with basic aminoacid, e.g. with arginine, lysine or histidine.

19 Claims, No Drawings

USE OF RIFAMYCIN SV AND ITS RELATED SALTS IN THE TREATMENT OF RHEUMATOID ARTHRITIS, AND RELATED FORMULATIONS SUITED FOR THE PURPOSE

DESCRIPTION OF THE INVENTION

The present invention concerns a new use of rifamycin SV in the treatment of rheumatoid arthritis, and analogous pathologic affections, by an intra-articular injection of rifamycin SV itself, preferably in a salified form. All the operations pertaining to the preparation of the salts as per re, with inclusion of their purification, their formulation into pharmaceutical dosage forms suited for its administration, and/or of their packaging into containers suited for administration shall be covered by the term "use", to be intended according to the present invention.

Rifamycin SV has been used for over 15 years in human and veterinary medicine as a therapeutic agent in all the range of infections due to Gram-positive and Gram-negative pathogens, Mycobacterium tuberculosis and Mycobacterium leprae.

All the pathologic conditions, in which rifamycin SV is used, are exclusively represented by all diseases due to an infectious causative factor, that can be briefly summarized as follows:

1. skin and soft tissue infections;
2. surgical infections;
3. ear, nose and throat infections;
4. bronchopulmonary and pleural infections;
5. liver and biliary tract infections;
6. tuberculous infections;
7. various infections (sty, paradental abscess, urethritis, etc.);
8. leprosy.

A new therapeutic activity of rifamycin SV has now been discovered; actually, intra-articular injections of said compound, or of its related salts, given into the joints of patients affected with rheumatoid arthritis, have been leading to a rapid resolution of the pathologic condition as well as to the patient's complete cure.

All commercially available solutions of rifamycin SV contain, in addition to the antibiotic in the form of a sodium salt, also a certain quantity of sodium ascorbate (added to the purpose of preventing the conversion of rifamycin SV into a rifamycin S solution) and, moreover, relevant quantities of polyvinylpyrrolidone added to the purpose of increasing the scarce local tolerability of the injection, and make therefore the antibiotic more available.

In fact, all aqueous solutions of rifamycin SV sodium salt, used up-to-now for all known therapeutic applications, have been observed to be scarcely suited for an intra-articular injection. Said solutions, actually, require the presence of polyvinylpyrrolidone, necessary not only to attain a sufficient concentration of said salt, intrinsically scarcely soluble in water, but also to increase the antibiotic bioavailability. Said characteristic, usually positive in a drug, represents a marked inconvenience to the purposes of the therapeutic procedure which is the object of the present invention, being ascertained that the higher the permanence of rifamycin SV in the joint, into which it has been injected, the more rapid the resolution of the pathologic condition.

It has been found for the purpose that rifamycin SV salts, in particular sodium salt, can be prepared in a substantially anhydrous form, for example through lyophilyzation; said salts, after addition of a suited quantity of distilled water, provide sterile solutions to be used extemporaneously. The related lyophilyzed ampuls, containing the antibiotic as sodium salt in the dry state, can be preserved for years at room temperature. In the case of the lyophilyzation process the aqueous solutions of rifamycin SV, resulting from the salification of the antibiotic with $NaHCO_3$ or NaOH in such a quantity as to attain a ph ranging between 7 and 8, shall never be brought over a temperature of $+4°$ C., and be thereafter frozen at $-35°$ C. as rapidly as possible.

No special caution is required in the subsequent lyophilyzation process.

Therefore the invention also concerns pharamaceuticl formulations of rifamycin SV salts in a substantially anhydrous form, containing no additives, suited for the preparation of solutions to be injected intra-articularly for the above mentioned treatment of rheumatoid arthritis.

The aqueous solutions of rifamycin SV salts with basic amino-acids, such as arginine, lysine, histidine, asparagine, etc., proved particularly useful for the therapeutic applications of the invention as per re.

Said salts, markedly more water-soluble than the sodium salt, are characterized by an unsatisfactory bioavailability, and remain therefore in the affected joint for a length of time sufficient to obtain the desired therapeutic effect.

Rifamycin SV salts with histidine, lysine and arginine prove very typical in this connection since their 20 percent aqueous solutions are characterized by a pH 6.4–6.7 perfectly suited both for the preservation of the antibiotic and for the intra-articular injection.

Said solutions, presenting with a pH between 6.5 and 7, are markedly more stable than the sodium salt solutions. After lyophilyzation, that can be carried out on the other hand with no special precautions, the salts of basic aminoacids with rifamycin S can be long preserved, easily providing ready-for-use extemporaneous solutions after addition of the suited quantities of distilled water.

A further object of the present invention consists therefore in pharmaceutical formulations represented by basic aminoacids salts with rifamycin SV, in a lyophilyzed form, suited for an intra-articular injection for the above mentioned treatment of rheumatoid arthritis.

The arginine salt of rifamycin SV proved particularly useful for the purpose because of its optimal water solubility properties.

Its 10 percent aqueous solution shows a pH 6.7; its local tolerability, assessed following a 60-mg injection given once daily for three consecutive days into the rabbit's spinal sac, versus equal quantities of commercial solutions of rifamycin SV, proved optimal and definitely better than that observed in the case of commercial solutions.

According to the present invention the rifamycin SV salts with basic aminoacids are obtained dissolving in water stoichiometric quantities of the two components, filtering the resulting solution and precipitating thereafter the salt with a nonsolvent, eg isopropanol, or eliminating water from the same solution, eg by lyophilyzation.

The below reported example illustrates the procedure of the invention, constituting however no limitation to the same.

EXAMPLE 12.5 (71.8 mmoles) of L-arginine and 50 g (71.8 mmoles) of rifamycin SV are dissolved in 200 ml of water for injectable preparations, under vacuum. The resulting solution is filtered under vacuum, under sterile conditions, and transferred thereafter into a lyophilyzer and cooled down at −35° C.

The resulting solution is kept as said temperature for three hours, before the under vacuum phase. The phase of primary drying, ie bringing the heating plate to 0° C., is started when the vacuum desired value is obtained, ie 0.1 Torr. This phase has a 24-hour duration. The secondary drying, wherein the plate is kept at room temperature, has a 3-hour duration. The final humidity of the product ranges on an approximate 1 percent level. The salts of L-lysine and L-histidine are prepared according to the same scheme, starting from 1.050 g and 1.113 g of the two aminoacids respectively.

The thin layer chromatography of the salts, obtained according to the above mentioned procedure (60 $F_{254}$ silica gel plates, Merck, 10×10) with a 3:1 chloroform-methanol eluent, enables to obtain the following $R_f$:

rifamycin SV salt with arginine: 0.54
rifamycin SV salt with histidine: 0.46
rifamycin SV salt with lysine: 0.48

The elemental analyses of the salts as per re have been providing the following values:

(a) L-arginine salt for $C_{43}H_{61}N_5O_{14}$ (MW 871.96)
%Calc.: C=59.23; H=7.05; N=8.03
%Found: C=58.85; H=6.93; N=7.85

(b) L-histidine salt:

for $C_{43}H_{56}N_4O_{14}$ (MW 852.91)
%Calc.: C=60.55; H=6.62; N=6.57
% Found: C=59.88; H=6.45; N=6.48

(c) L-lysine salt for $C_{43}H_{61}N_3O_{14}$ (MW 843.94) %Calc.: C=61.19; H=7.28; N=4.98 % Found: C=60.80; H=7.41; N=4.71

The solubility of the salts of histidine and lysine is high in water and methanol, good in ethanol and acetone, and practically nil in isopropanol, ether, benzene, ethyl acetate. The arginine salt, highly soluble in water, methanol and acetone, is also sparingly soluble in ethyl acetate and chloroform.

Bioavailability Data

The scarce bioavailability of the salts, according to the invention, has already been mentioned. Said salts enable to obtain (after an intra-articular injection) high concentrations of rifamycin in the synovial fluid for times of 24–48 hours after the injection; in the meantime, rifamycin attains its maximal serum concentration after 30 minutes, and still results to be present in minimal quantities 24 hours after the injection. The rifamycin levels, present in the biological fluids of treated patients, were assayed by high pressure liquid chromatography (HPLC), a method more reliable and reproducible than the ultraviolet or microbiological method.

The synovial fluid samples were directly injected into the chromatograph after precipitation of the proteins with acetonitrile on the other hand, the serum samples had to be previously extracted with ethyl acetate at an acid pH.

Only rifamycin SV is present in the synovial fluid while the serum also contains rifamycin S.

A Hewlett Packard chromatograph is used, model 104 B, fitted with a fixed wave length detector (254 nm); RP 18 (10 mc) column, 25-cm length, 4-cm diameter.

The following eluent is used: (A) an 80:20 mixture of 0.01 M phosphate buffer at pH 7 and acetonitrile; (B) acetonitrile. The gradient shifts from the 10 percent of B to the 70 percent of B within 15 minutes; the flow is 1.6 ml/minute.

The temperature of the oven is 35° C.; that of the eluent A is 60 percent and the one of the eluent B 40 percent.

Preparation of the Standard Line

Rifamycin SV and its oxidized form, ie rifamycin S, are used as standard.

In order to establish the standard lines in the synovial fluid, 500 mg of each single compound are dissolved in one liter exactly of a 1:1 water-methanol mixture.

The two absorption lines are made up injecting 5 mcl, 10 mcl and 15 mcl of said solutions into the chromatograph.

The previous solutions are ten-fold diluted in the case of sera standard lines; the above mentioned operations are thereafter repeated.

Determination of rifamycin SV in the synovial fluid

This determination is directly carried out on the deproteinized synovial fluid. 200 mcl of sample are introduced into a centrifuge test tube, and added with 2 ml of acetonitrile.

The resulting solution is stirred, and allowed to decant; 20 mcl of supernatant fluid are thereafter injected into the chromatograph. The samples are analyzed immediately in order to prevent the oxidation of rifamycin SV into rifamycin S.

Determination of Rifamycin in the Serum 2 ml of serum are added with an equal volume of a buffer solution at pH 1.71. Said solution is prepared mixing 200 ml of N acetic acid, 200 ml of N NaOH, 220 ml of N hydrochloric acid, and made thereafter to the exact volume of one liter with water. The resulting solution is extracted two times with 10 ml of ethyl acetate. The organic phase is brought to dryness, and resumed thereafter with 500 mcl of acetonitrile. 20 mcl of said solution are injected for the analysis.

Table 1 summarizes the rifamycin levels in the serum and in the synovial fluid of patients given a 500-ml intra-articular injection of L-arginine salt of rifamycin SV. The data are expressed as mcg/ml.

TABLE 1

| | | | | TIMES | | | | |
|---|---|---|---|---|---|---|---|---|
| 15' | 30' | 1h | 2h | 4h | 6h | 8h | 24h | 48h |
| | | | | Serum Levels | | | | |
| — | 1.54 ± 0.2 | 0.95 ± 0.42 | 0.93 ± 0.16 | 0.583 ± 0.09 | 0.527 ± 0.38 | 0.318 ± 0.21 | 0.221 ± 0.12 | 0.250 ± 0.25 |
| | | | | Synovial Levels | | | | |

TABLE 1-continued

| | | | | TIMES | | | | |
|---|---|---|---|---|---|---|---|---|
| 15' | 30' | 1h | 2h | 4h | 6h | 8h | 24h | 48h |
| 4930 ± 550 | 2890 ± 510 | 1360 ± 380 | 860 ± 250 | 373 ± 170 | 76 ± 40 | 47 ± 20 | 26 ± 15 | 9 ± 8 |

Table 2, on the other hand, points out the pattern differences, to the purpose of the treatment of rheumatoid arthritis according to the invention, between the rifamycin SV sodium salt and the rifamycin SV salts with basic aminoacids. The data shown in Table 2 (that represent the mean of eight determinations, and are expressed as mg/ml) compare the levels of rifamycin in the synovial fluid of patients given an intra-articular injection with quantities of sodium salt and arginine salt equivalent to 500 mg of rifamycin SV; said data demonstrate the marked superiority of the arginine salt.

TABLE 2

| 5' | 1h | 2h | 4h | 8h |
|---|---|---|---|---|
| | | Sodium Salt | | |
| 6.7±0.2 | 1.53±0.49 | 0.485±0.18 | 0.439±0.18 | 0.140±0.067 |
| | | Arginine Salt | | |
| 7.16±2.1 | 3.85±0.8 | 1.73±1 | 0.75±0.3 | 0.173±0.1 |

The observation that in the monoarthritic guinea-pig (gamma-globulin arthritis) rifamycin arginine salt levels, 10 times higher than in the case of rifamycin sodium salt, can be observed following an intra-articular administration of either rifamycin sodium salt or arginine salt, proves in full agreement with the above mentioned datum.

Clinical Data

The effects of intra-articular injections of rifamycin SV solutions in rheumatoid synovitis were assessed in two clinical trials, one carried out according to an open technique and the other one according to a double-blind experimental design. A total of 35 patients was treated, with an intra-articular injection of 200–500 mg weekly, for a maximum of 10 weeks. The patients were followed up for three years. The following laboratory diagnostic tests were made weekly on the synovial fluids: white blood cell differential count, RA test, Waaler-Rose test, latex test, immunoglobulins, T and B lymphocytes, $C_3$ and $C_4$ levels, glucose, acid phosphatase.

Bioptic examinations were carried out both before and after various months (1–18) after the start of the treatment.

The exudate proved to be completely disappeared after the third and within the tenth instillation of rifamycin SV. Said exudate reappeared only in two patients, i.e. in one case 2 months, and in other case twelve months respectively after discontinuation of the treatment.

A significant drop of total leukocytes, polymorphocyte percentage and RA cells was observed at the end of the treatment. No variations were observed in the immunological parameters. The knees of the patients treated in the above mentioned manner with rifamycin SV showed the following variations from a histological standpoint: reduction of synovial cell infiltrates, increase of newly-formed connective tissue, surrounding areas with a residual hyperplastic synovia, depositions of a new partially organized fibrin.

No significant changes were observed in the control patients given saline.

In a second clinical experimental course, 75 patients, presenting with persistent effusions in one or both knees were given 500 mg of rifamycin SV (in the form of a L-arginine salt) every seven days, still by intra-articular injection.

A complete subsidence of the effusions and a marked clinical improvement were observed in seventy-two of said patients; 28 of them were followed up for 1–6 months, 10 for 7–12 months, 16 for 1–2 years and 15 for 2–5 years. Only 3 patients presented with an effusional relapse 1–6 months after the start of the treatment. 12 out of 72 patients required 1–3 infiltrations; 33 required 4–6 infiltrations and 27 patients 7–12 infiltrations in order to induce an effusion subsidence. Only one patient did not respond to 12 infiltrations. The number of the infiltrations was strictly related with the activity of the local synovitis ($P<0.05$). The gradual regression of the effusion proved related with changes in synovial fluid anomalies, i.e. significant decrease of leukocytes ($P<0.001$) and increase of the $C_3$ and $C_4$ complemental fractions ($P<0.005$).

Rifamycin SV produced an initial local pain in the majority of the patients, and a local retarded painful reaction in 28 out of 72 patients. Two of the 75 patients had to stop the treatment because of the above mentioned untoward side effect. Infiltrations of rifamycin SV L-arginine salt into joint sites other than the knee (wrist, hand's metacarpophalangeal and interphalangeal joints, tibiotarsal joints, etc, for an overall total of 300 joints approximately) demonstrate the potent analgesic and anti-inflammatory activity of the drug: the treatment results in a marked reduction, and quite often in a complete subsidence, of morning stiffness, in an increased grip strength ranging between 60 and 100 percent levels together with an overall improvement of joint function. In the course of the treatments given for rheumatoid arthritis, and other forms of arthritis, by means of rifamycin SV intra-articular injections, the inhibiting activity of rifamycin SV was demonstrated on cultures of synovial membrane fragments withdrawn by a needle biopsy, made for diagnostic purposes in patients presenting with a suspected rheumatoid arthritis.

Moreover also the scarce diffusion of rifamycin SV, directly injected into the joint, was observed, and consequently its possible inhibiting activity on the chemical mediators of inflammation and lymphokines.

For the attainment of said results rifamycin SV, preferably in the form of a salt, had to be injected directly into the joint cavity so as to attain such high concentrations otherwise unattainable with a systemic use of the drug.

Rifamycin SV persists in the affected joint such a long time as to enable the dosage schedule of one 200/1000-mg once weekly, as demonstrated by the previously mentioned kinetic investigation carried out on the synovial fluid.

We claim:
1. The salt of rifamycin SV with a basic aminoacid.
2. The salt of rifamycin SV with arginine.
3. The salt of rifamycin SV with lysine.

4. The salt of rifamycin SV with histidine.

5. The method of treatment of a joint affected by rheumatoid arthritis, which consists of administering to a patient affected with a form of rheumatoid arthritis in a joint by means of intra-articular injections into the affected joint of rifamycin SV or salt thereof in the amount of 200–1000 mgs per injection.

6. The method according to claim 5, wherein the injection is administered once per week.

7. The method according to claim 5, wherein an aqueous solution of rifamycin SV, in a salified form, is injected into the affected joint of said patient.

8. The method according to claim 5, wherein an aqueous solution of a salt of rifamycin SV with a basic aminoacid is injected into the affected joint.

9. The method according to claim 8, wherein the rifamycin SV salt is the arginine salt.

10. The method according to claim 8, wherein the rifamycin SV salt is the lysine salt.

11. The method according to claim 8, wherein the rifamycin SV salt is the histidine salt.

12. The method according to claim 7, wherein the aqueous solution of rifamycin SV, in a salified form, is free from additives.

13. The method according to claim 7, wherein the aqueous solution is prepared at the very moment of use by dissolving in water the desired dose of a substantially anhydrous salt of rifamycin SV.

14. A formulation for the treatment of rheumatoid arthritis by an intra-articular injection of rifamycin SV, consisting of an aqueous solution of 200–1000 mgs. of a rifamycin SV salt with a basic aminoacid.

15. A formulation according to claim 14, wherein the basic aminoacid is arginine.

16. A formulation according to claim 14, wherein the basic aminoacid is lysine.

17. A formulation according to claim 14, wherein the basic aminoacid is histidine.

18. A formulation according to claim 14, wherein the aqueous solution is free from additives.

19. A formulation according to claim 14, wherein the aqueous solution is prepared extemporaneously dissolving in water the substantially anhydrous salt of rifamycin SV with a basic aminoacid.

* * * * *